(12) United States Patent
Boukhvalova et al.

(10) Patent No.: US 9,149,508 B1
(45) Date of Patent: Oct. 6, 2015

(54) VACCINATION BY CIRCUMVENTING PREEXISTENT IMMUNITY

(71) Applicant: Sigmovir Biosystems, Inc., Rockville, MD (US)

(72) Inventors: Marina S. Boukhvalova, Potomac, MD (US); Jorge C. G. Blanco, Washington, DC (US)

(73) Assignee: Sigmovir Biosystems, Inc., Rockville, MD (US)

( * ) Notice: Subject to any disclaimer, the term of this patent is extended or adjusted under 35 U.S.C. 154(b) by 330 days.

(21) Appl. No.: 13/660,035

(22) Filed: Oct. 25, 2012

Related U.S. Application Data

(60) Provisional application No. 61/551,907, filed on Oct. 26, 2011.

(51) Int. Cl.
  *C07K 14/765* (2006.01)
  *A61K 38/21* (2006.01)
  *A61K 39/00* (2006.01)

(52) U.S. Cl.
  CPC ............ *A61K 38/212* (2013.01); *A61K 38/217* (2013.01); *A61K 2039/55516* (2013.01)

(58) Field of Classification Search
  None
  See application file for complete search history.

(56) References Cited

U.S. PATENT DOCUMENTS 6,977,074 B2 * 12/2005 Kundig et al. ............... 424/93.7
2002/0165176 A1 * 11/2002 Haynes et al. .................. 514/44

OTHER PUBLICATIONS

Albrecht, P. et al., Persistence of Maternal Antibody in Infants Beyond 12 Months: Mechanism of Measles Vaccine Failure, The Journal of Pediatrics, Nov. 1977, 715-718.
Arulanandam, B.P. et al., Neonatal Administration of IL-12 Enhances the Protective Efficacy of Antiviral Vaccines, The Journal of Immunology, 2000, 164:3698-3704.
Booy, R. et al., Immunogenicity of Combined Diphtheria, Tetanus, and Pertussis Vaccine Given at 2, 3, and 4 Months Versus 3, 5, and 9 Months of Age, The Lancet, Feb. 29, 1992, 339(8792):507-510.
Burstyn, D.G. et al., Serological Response to Filamentous Hemagglutinin and Lymphocytosis-Promoting Toxin of Bordetella pertussis, Infection and Immunity, Sep. 1983, 41(3):1150-1156.
Daeron, M., Fc Receptor Biology, Annual Review of Immunology, 1997, 15:203-234.
Dagan, R. et al., Immunization Against Hepatitis A in the First Year of Life: Priming Despite The Presence of Maternal Antibody, The Pediatric Infectious Disease Journal, Nov. 2000, 19(11):1045-1052.
Daum, R.S. et al., Serum Anticapsular Antibody Response in the First Week after Immunization of Adults and Infants with the Haemophilus Influenzae Type B-Neisseria Menigitidis Outer Membrane Protein Complex Conjugate Vaccine, The Journal of Infectious Diseases, Dec. 1991, 164(6):1154.
Fernandes, D.M., Characterization of MHC Class II-Presented Peptides Generated from an Antigen Targeted to Different Endocytic Compartments, European Journal of Immunology, 2000, 30:2333-2343.
Fitzgerald, J.C. et al., A Simian Replication-Defective Adenoviral Recombinant Vaccine to HIV-1 Gag, The Journal of Immunology, 2003, 170:1416-1422.
Grimaldi, C.M. et al., B Cell Selection and Susceptibility to Autoimmunity, The Journal of Immunology, 2005, 174:1775-1781.
Hangalapura, B.N. et al., Delivery Route, MyD88 Signaling and Cross-Priming Events Determine the Anti-Tumor Efficacy of an Adenovirus Based Melanoma Vaccine, Vaccine, 2011, 29:2313-2321.
Kimata, H. et al., Selective Inhibition of Spontaneous IgE and IgG4 Production by Interleukin-8 in Atopic Patients, Blood, Jun. 1, 1995, 85(11):3191-3198.
Knudsen, K.M. et al., Child Mortality Following Standard, Medium or High Titre Measles Immunization in West Africa, International Journal of Epidemiology, 1998, 25(3):665-673.
Majewska, M. et al., Rola Receptorow Toll-Podobnych (TLR) w Odporności Wrodzonej i Nabytej Oraz ich Funkcja w Regulacji Odpowiedzi Immunologicznej, Postepy Hig Med Dosw. (online), 2006, 60:52-63. (Poland—English Abstract).
Marsh, C.B. et al., Regulation of Monocyte Survival in Vitro by Deposited IgG: Role of Macrophage Colony—Stimulating Factor, The Journal of Immunology, 1999, 162:6217-6225.
Nguyen, T.V. et al., High Titers of Circulating Maternal Antibodies Suppress Effector and Memory B-Cell Responses Induced by an Attenuated Rotavirus Priming and Rotavirus-Like Particle-Immunostimulating Complex Boosting Vaccine Regimen, Clinical and Vaccine Immunology, 2006, 13(4):475-485.
Stubbe, B.G. et al., "Programmed Polymeric Devices" for Pulsed Drug Delivery, Pharmaceutical Research, Oct. 2004, 21(10):1732-1740.
Tobin, G.J. et al., Deceptive Imprinting and Immune Refocusing in Vaccine Design, Vaccine, 2008, 26:6189-6199.
Troisi, C.L. et al., Immunization of Seronegative Infants with Hepatitis A Vaccine (Havrix; SKB): A Comparative Study of Two Dosing Schedules, Vaccine, 1997, 15(15):1613-1617.
Wallace, P.K. et al., Role of Fcγ Receptors in Cancer and Infectious Disease, Journal of Leukocyte Biology, Jun. 1994, 55:816-826.

* cited by examiner

*Primary Examiner* — Yunsoo Kim
(74) *Attorney, Agent, or Firm* — George W. Cox

(57) ABSTRACT

Methods and compositions are disclosed for improving vaccination in a subject with preexistent antibodies to the antigenic component of the immunizing vaccine. By temporarily sequestering, disabling, and/or suppressing preexistent antibodies and/or Fc-mediated mechanisms according to the various example embodiments, the target antigenic component of a vaccine has an increased opportunity to enter antigen-presenting cells through the same pathway that it would use in seronegative subjects. A balanced immune environment is thereby restored and B cells are properly activated to produce antigen-specific antibodies following vaccination.

8 Claims, 2 Drawing Sheets

VACCINATION BY CIRCUMVENTING PREEXISTENT IMMUNITY

CROSS-REFERENCE TO RELATED APPLICATIONS

This application claims the benefit of U.S. Provisional Patent Application Ser. No. 61/551,907, filed Oct. 26, 2011, which is hereby incorporated by reference in its entirety.

BACKGROUND OF THE INVENTION

The present invention relates to vaccination in a subject that has preexistent immunity. While the invention is subject to a wide range of applications, it is especially suited for vaccination in animals and humans against infectious diseases, autoimmune disorders, and cancer.

Preexistent immunity suppresses the efficacy of vaccination against a wide variety of antigens. This phenomenon has been most widely studied in connection with the ability of maternal antibodies to suppress infant responses to vaccination against infectious diseases. Significantly reduced seroconversion rates and/or mean antibody titers in infants immunized in the presence of maternal antibodies were initially reported during vaccination against measles virus more than 25 years ago (Albrecht et al., J. Pediatr. 91:715, 1977). Other live vaccines, including oral polio, varicella-zoster, influenza, and oral human rotavirus vaccines are subject to maternal antibody-mediated immunosuppression (Chan et al., Vaccine 29:1242, 2011; Karron et al., Pediatr. Infect. Dis. J. 14:10, 1995; Perkins et al., Br. Med. J. 1:1083, 1959). Contrary to the initial thought of some skilled in the art, subunit and inactivated vaccines are also inhibited by preexistent antibodies. The efficacy of pertussis vaccine (Burstyn et al., Infect. Immun. 41:1150, 1983; Englund et al., Pediatrics 96:580, 1995), haemophilus influenza type B conjugate vaccines (Claesson et al., J. Pediatr. 114:97, 1989; Daum et al., J. Infect. Dis. 164:1154, 1991), hepatitis A vaccine (Dagan et al., Pediatr. Infect. Dis. J. 19:1045, 2000; Kanra et al., Turk. J. Pediatr. 42:105, 2000; Troisi et al., Vaccine 15:1613, 1997), and tetanus and diphtheria toxoids vaccines (Barr et al., Lancet 1:6, 1950; Bjorkholm et al., Pediatr. Infect. Dis. J. 14:846, 1995; Booy et al., Lancet 339:507, 1992; Sarvas et al., J. Infect. Dis. 165:977, 1992) is reduced in the presence of maternal antibodies. The problem is not limited to the newborn population. Vaccination of individuals of any age with antigens delivered via pathogen-derived vectors (for example, adenovirus-based vaccines) is subject to immunosuppression by preexistent antibodies to that vector (Casimiro et al., J. Virol. 77:6305, 2003; Fitzgerald et al., J. Immunol. 170:1416, 2003). As pathogen-vectored vaccines are currently being developed not only against infectious diseases but also against cancer and autoimmune dysfunction (Hangalapura et al., Vaccine 29:2313, 2011; Spohn et al., J. Immunol. 178:7450, 2007), vaccines against these disorders are also subject to antibody-mediated immunosuppression. Immunosuppression by preexistent antibodies also impacts the veterinary field. Vaccination of livestock, poultry, and horses against debilitating and life-threatening diseases, including pandemic influenza, Newcastle disease virus, and rotavirus is subject to antibody-mediated immunosuppression in the presence of maternal antibodies (Maas et al., Avian. Pathol. 40:87, 2011; Nguyen et al., Clin. Vaccine Immunol. 13:475, 2006; Perozo et al., Avian Dis. 52:253, 2008; Ryan et al., Clin. Vaccine Immunol. 17:1896, 2010; Wesley et al., Vaccine 22:3427, 2004).

Several mechanisms have been proposed to explain the inhibitory effect of maternal antibodies on vaccination. Included among the proposed mechanisms are: neutralization of live viral vaccines rapidly after injection (Albrecht et al., J. Pediatr. 91:715, 1977), epitope masking that prevents antigen binding by naive B cells (Heyman et al., Springer Semin. Immunopathol. 23:421, 2001), elimination of immune complexes by Fc-dependent endocytosis (McKendall et al., J. Infect. Dis. 151:464, 1985; Wallace et al., J. Leukoc. Biol. 55:816, 1994), and colligation of the B cell receptor with FcγRIIB leading to an inhibition of B cell responses (Daeron et al., Annu Rev. Immunol. 15:203, 1997). Some of these theories, such as the epitope-specific masking of B cells, are better supported by available clinical and experimental data than others (Jelonek et al., J. Infect. Dis. 174:866, 1996; Kurikka et al., Pediatr. Infect. Dis. J. 15:530, 1996; Nohynek et al., Pediatr. Infect. Dis. J. 18:25, 1999; Panpitpat et al., Bull. World Health Organ. 78:364, 2000). Additional mechanisms may explain the phenomenon of antibody-mediated immunosuppression.

Counteracting or circumventing the immunosuppressive effect of preexistent immunity on vaccination would greatly benefit public health and agricultural resources. However, efficient methods and vaccine compositions for improving vaccination of subjects with preexistent immunity have not been developed. Cytokine and toll-like receptor-stimulating molecules have been tried in animal models in the context of vaccine formulations targeted to neonates (Arulanandam et al., J. Immunol. 164:3698, 2000; Ishii et al., Gene Ther. 6:237, 1999; Kovarik et al., Arch. Immunol. Ther. Exp. (Warsz) 49:209, 2001; Pertmer et al., Vaccine 19:1764, 2001). DNA- and viral-vectored delivery of vaccine antigens to infants have been proposed but the immunosuppressive effect of maternal antibodies limits the efficacy of these approaches as well (Mahon et al., Curr. Med. Chem. 8:1057, 2001). Based on the epitope-masking theory, it was hypothesized that increasing the dose of vaccine antigen would circumvent inhibition by maternal antibodies as excess antigenic epitopes would remain free of maternal antibodies and become more accessible to infant B cells. Indeed, higher dose hepatitis A vaccine or measles virus vaccine enhanced serological responses in infants vaccinated in the presence of maternal antibodies (Dagan et al., Pediatr. Infect. Dis. J. 19:1045, 2000; Cutts et al., Vaccine 12:1311, 1994). However, excess mortality was seen among infants vaccinated with high doses of live measles vaccine (Knudsen et al., Int. J. Epidemiol. 25:665, 1996). Thus, there remains a need for safe and effective approaches to enhancing the efficacy of vaccination in subjects with preexistent immunity.

SUMMARY OF THE INVENTION

Antibody production by B cells is a delicate process dependent on a precise balance between proper activation and apoptosis of B cells (Grimaldi et al., J. Immunol. 174:1775, 2005). A different local immune environment is created during antigen introduction in free form versus antigen introduction as an antigen-antibody complex. Antigen-antibody complex does not normally permeate antigen-presenting cells (APC) directly. Instead, antigen-antibody complex enters APC via the mechanism of Fc receptor-mediated endocytosis. Interaction of immune complexes with FcγR (and FcγR crosslinking) on human monocytes and myeloid dendritic cells induces a panel of cytokines and chemokines, including IL-8, MCP-1, and GM-CSF (Marsh et al., J. Immunol. 162: 6217, 1999; Marsh et al., J. Immunol. 157:2632, 1996; Marsh et al., J. Immunol. 155:3161, 1995; Marsh et al., J. Immunol.

158:1078, 1997). As B cell function and survival are dependent on pro-inflammatory cytokines and chemokines (Kimata et al., Blood 85:3191, 1995; McGettrick et al., Br. J. Haematol. 139:185, 2007), a switch in the local immune environment from direct entry into APC to Fc receptor-mediated endocytosis would have a large impact on B cell function. Interaction with antigenic determinants that engage pattern-recognition receptors on APC and B cells also regulates cytokine/chemokine responses with subsequent activation/dampening of immune function (Majewska et al., Postepy. Hig. Med. Dosw. (Online) 60:52, 2006). The absence of such interaction when antigen is presented as a complex with immunoglobulins would circumvent normal pathways. Finally, processing of immunoglobulin-associated antigen is different from that of the free antigen and can lead to generation of a different subset of epitopes, some with suboptimal immune function (Fernandes et al., Eur. J. Immunol. 30:2333, 2000).

We have observed that besides being masked or sequestered in the presence of preexistent antibodies, antigens are presented to the immune system in a different form in the presence of preexistent antibodies (the latter of which triggers an aberrant immune reaction that culminates in improper B cell activation following vaccination). Accordingly, one object of the invention is to provide methods of minimizing the imbalance in the immune environment that is elicited during vaccination in the presence of preexistent immunity. Another object of the invention is to provide vaccine compositions that improve the immune response to the antigenic component of the vaccine in subjects with preexistent immunity. By temporarily sequestering, disabling, and/or suppressing preexistent antibodies and Fc-mediated mechanisms according to the various representative objects, embodiments, and aspects of the invention, the target antigenic component of a vaccine has an increased opportunity to enter APC through the same pathway that it would use in seronegative subjects. A balanced immune environment is thereby restored and B cells are properly activated to produce antigen-specific antibodies following vaccination (FIG. 1).

In one representative embodiment, a method is provided for vaccination in a subject comprising administering at least one agent that circumvents (that is, for example, disables, sequesters, and/or suppresses) preexistent immunity against the antigenic component of the vaccine. In one aspect, the preexistent immunity is preexistent antibodies directed to the antigenic component of the vaccine.

In another representative embodiment, a method is provided for improving vaccination in a subject that has preexistent antibodies directed to the antigenic component of the vaccine by administering to the subject a vaccine and at least one agent that circumvents the immunosuppressive effects of the preexistent antibodies on vaccination.

In another representative embodiment, a method is provided for improving vaccination in a subject by administering simultaneously to the subject a vaccine and at least one agent that can bind to preexistent antibodies directed to the antigenic component of the vaccine. In one aspect, agents that may be used include, for example, those that can bind to the antigen-recognition (Fab) region of preexistent antibodies (paratopes) and prevent preexistent antibodies from associating with their cognate ligand. In another aspect, agents that may be used include, for example, those that can bind to the Fc region of preexistent antibodies and prevent already-formed antigen-antibody complexes from interacting with the Fc receptors on APC.

In another representative embodiment, the vaccine is administered before at least one of the aforementioned agents and, optionally, the vaccine is administered with at least one device or method for the delayed-release of the vaccine. Alternatively, at least one of the aforementioned agents is administered before the vaccine and, optionally, the agent(s) is administered with at least one device or method for the delayed-release of the agent(s). If desired, at least one of the agents may be administered within 24 hours before the administration of the vaccine.

In another representative embodiment, a vaccine composition is provided that comprises an antigen and a means for circumventing (that is, for example, an agent capable of disabling, sequestering, and/or suppressing) preexistent immunity against the antigen. In one aspect, the antigen may be, for example, live pathogen, disease-associated native protein or a fragment thereof, or disease-associated recombinant protein or a fragment thereof. In another aspect the means for circumventing preexistent immunity may be, for example, an inactivated whole pathogen, at least one pathogen component, at least one molecule that binds immunoglobulin, and/or at least one agent that blocks Fc receptors on endogenous Fc-receptor-bearing cells.

In another representative embodiment, a vaccine composition is provided that improves immunity against the antigenic component of the vaccine in a subject having preexistent antibodies directed to the antigenic component of the vaccine. In one aspect of the embodiment, the vaccine composition may include an antigen and an inactivated whole pathogen. In another aspect of the embodiment, the vaccine composition may include an antigen and at least one pathogen component. Pathogen components that may be used include, for example, native proteins or fragments thereof (including peptides and polypeptides) and recombinant proteins or fragments thereof (including peptides and polypeptides). In another aspect of the embodiment, the vaccine composition includes an antigen and at least one molecule that binds to immunoglobulin. Molecules that bind immunoglobulin may include, for example, native proteins or fragments thereof, recombinant proteins or fragments thereof, recombinant Protein A, native Protein A, recombinant Protein G, native Protein G, recombinant Protein A/G, native Protein A/G, recombinant antibody against the Fc region of immunoglobulin, native antibody against the Fc region of immunoglobulin, recombinant Fab fragment of antibody against the Fc region of immunoglobulin, native Fab fragment of antibody against the Fc region of immunoglobulin, recombinant Fab fragment of antibody against the Fab region or paratope of immunoglobulin, native Fab fragment of antibody against the Fab region or paratope of immunoglobulin, non-immunoglobulin blockers of the Fc region of immunoglobulin, and agents that bind to both the Fab region and Fc region of immunoglobulin. In an additional aspect, the vaccine composition may include an antigen and at least one agent that blocks Fc-receptor-bearing cells whereby either the inactivated whole pathogen or the pathogen component(s) can bind to preexistent antibodies that are directed to the antigenic component of the vaccine. In a further aspect of the embodiment, the vaccine composition may include an antigen and at least one agent that blocks Fc receptors on endogenous Fc-receptor-bearing cells. Agents that blocks Fc receptors on endogenous Fc-receptor-bearing cells may include, for example, proteins, glycoproteins, antibodies, peptides, oligosaccharides, fragments of all the aforementioned agents, and small molecules such as chemicals, biochemicals and pharmaceutical agents.

One skilled in the art would understand that kits and packages may be prepared comprising all or any combination of the vaccines, agents, and components described herein.

These and other objects are achieved in the invention.

The present invention overcomes a major disadvantage of current vaccination methods and compositions by providing methods and compositions that circumvent the immunosuppressive effect of preexistent immunity when, for example, maternal antibodies suppress de novo antibody production and when, for example, preexistent antibody to vectored vaccines interferes with the immunogenicity of delivered antigens.

There has thus been outlined, rather broadly, features of the invention in order that the detailed description thereof that follows may be better understood, and in order that the present contribution to the art may be better appreciated. There are, of course, additional features of the invention that will be described further hereinafter. Indeed, it is to be understood that both the foregoing general description and the following detailed description are exemplary and explanatory and are intended to provide further explanation of the invention as claimed.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception upon which this disclosure is based may readily be utilized as a basis for the designing of other methods, systems, kits, and compositions for carrying out the several purposes of the present invention. It is important, therefore, that equivalent constructions insofar as they do not depart from the spirit and scope of the present invention, are included in the present invention.

The accompanying drawings are included to provide a further understanding of the invention and are incorporated in and constitute a part of this specification, illustrate several embodiments of the invention, and together with the description serve to explain the principles of the invention.

BRIEF DESCRIPTION OF THE DRAWINGS

FIG. 1A shows the consequences of vaccination in a naive subject (that is, one without preexistent immunity to the antigenic component of a vaccine). FIG. 1B shows the consequences of vaccination in an immune subject (that is, one with preexistent immunity to the antigenic component of a vaccine). FIG. 1C shows the consequences of vaccination in a subject that was vaccinated using example embodiments of the invention.

FIG. 2 demonstrates that the efficacy of vaccination with live respiratory syncytial virus (RSV) in cotton rats with preexistent immunity is improved by inclusion of Streptococcal Protein G and ultraviolet light irradiated (inactivated) RSV (UV-RSV) in the vaccine composition. FIG. 2A shows the levels of virus in the lungs of cotton rats immunized with live RSV in the absence and presence of Protein G and/or UV-inactivated RSV. FIG. 2B shows the levels of anti-RSV IgG in the serum of cotton rats immunized with live RSV in the absence and presence of Protein G and/or UV-inactivated RSV. Cotton rats were infused with 0.2 ml anti-RSV serum (titer 1:2,600) or control serum and 24 hours later immunized intramuscularly with $10^4$ pfu of live RSV. Where indicated, the vaccine preparation also included 25 µg Protein G or UV-inactivated RSV (an equivalent of $10^4$ pfu) per animal. Twenty-eight days after immunization, all animals were challenged intranasally with RSV ($10^5$ pfu/animal) and sacrificed 4 days later for analysis of RSV viral titers in the lungs. Sera were collected for analysis of total anti-RSV IgG on days 1, 14, and 28 post-vaccination. Results shown are the mean±SEM for 5 animals per group. Results of one of two representative experiments are shown.

DETAILED DESCRIPTION OF THE INVENTION

Figure 1:
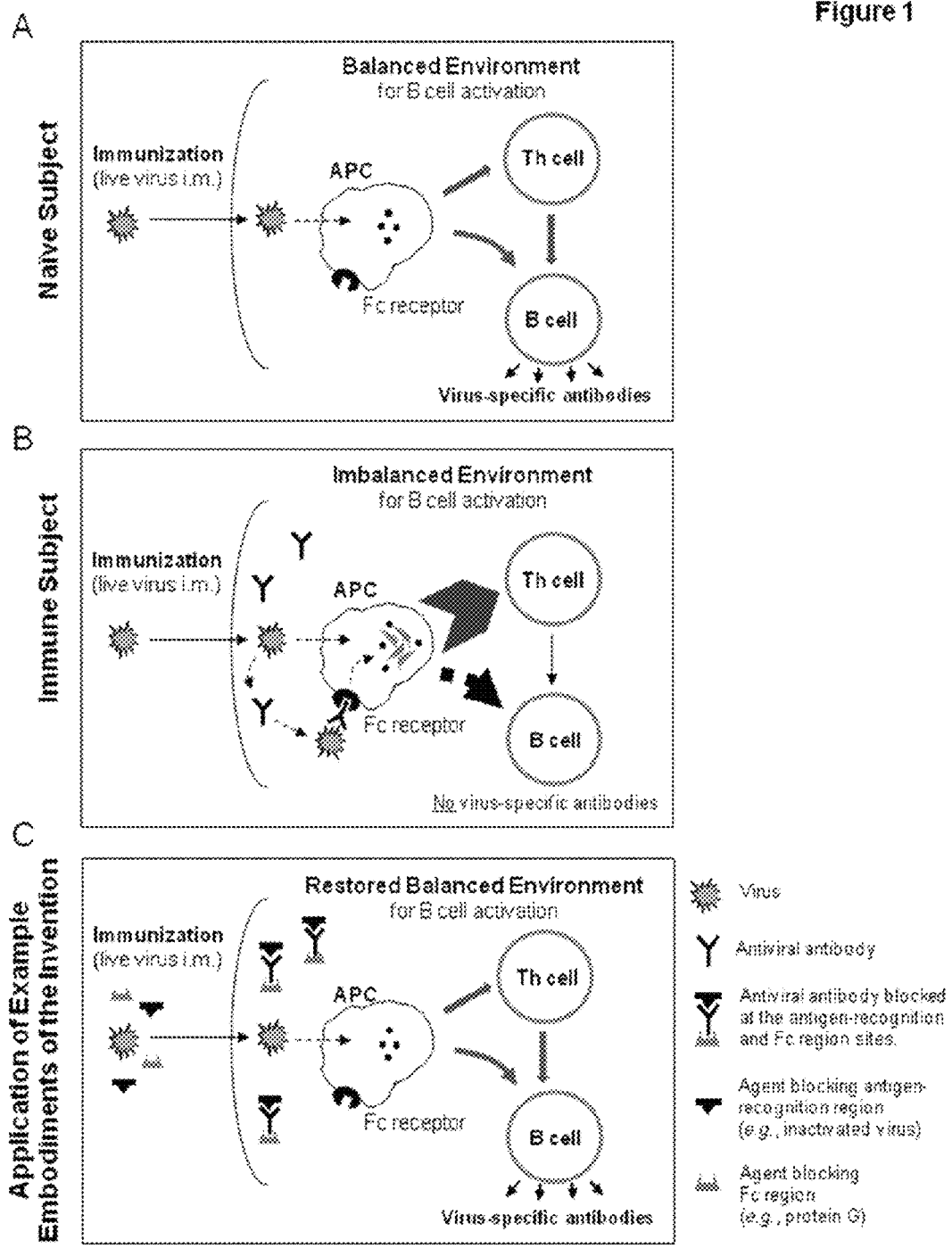
FIG. 1 depicts our model of the immunosuppressive effect of preexistent antibodies on vaccination and exemplary ways of circumventing the immunosuppressive effect to achieve improved vaccination in subjects with preexistent antibodies.

Provided herein are methods and compositions for improving vaccination in subjects with preexistent immunity directed against the antigenic component of the vaccine. Reference will now be made in detail to representative embodiments of the invention, examples of which are illustrated in the accompanying drawings.

FIG. 1A shows that in the absence of preexistent antibodies, antigen (for example, live virus administered intramuscularly (i.m.)) interacts directly with an antigen-presenting cell (APC) causing activation of cytokine production and antigen processing/presentation, which leads to appropriate T-helper (Th) cell and B cell stimulation. This is a balanced environment that culminates in the production of virus-specific antibodies. FIG. 1B shows that in the presence of preexistent antibodies, antigen enters APC as a complex with antibody through Fc receptor-mediated endocytosis. This results in a different type of antigen processing/presentation and cytokine production by APC, which leads to an imbalanced immune environment and subsequently the impaired production of virus-specific antibodies by B cells. In accordance with the invention, FIG. 1C demonstrates that the immunosuppressive effect of preexistent antibodies can be overcome by including in a vaccination method (or vaccine composition) one or more agents that block antigen-specific antibodies. Such agents may include, for example, agents that bind to the antigen-recognition (Fab) site on preexistent antibodies (for example, UV-inactivated virus) and agents that bind to the antibody Fc region (for example, Streptococcal Protein G). Once inside the vaccinated subject, these agents prevent antibody from interacting with its cognate ligand and Fc receptors on APC. With preexistent antibodies (and Fc-mediated mechanisms) temporarily disabled, sequestered, and/or suppressed, an antigen has an enhanced ability to engage the immune system as a free molecule (as in a seronegative subject), thereby restoring a balanced immune environment and leading to efficient and improved production of antigen-specific antibodies by B cells following vaccination.

One skilled in the art will recognize that the representative embodiments are applicable to vaccines against infectious diseases, cancer, and autoimmune disorders under various conditions including when maternal antibodies suppress de novo antibody production and when preexistent antibody to vectored vaccines suppress the immunogenicity of delivered antigens. Other embodiments of the invention may be directed to re-focusing the immune response to pathogens, cancer molecules, and molecules that influence autoinflammatory disorders. Often the epitopes predominantly recognized by an immune system are not the ones that elicit the most efficient or broad-acting immune response (Tobin et al., Vaccine 26:6189, 2008). These underrepresented epitopes may induce specific antibodies that are lower in quantity and/or avidity compared to antibodies against other immunodominant epitopes. Yet the presence of these antibodies may impact immunogenicity of the same epitopes when introduced in a context of a new vaccine. Vaccines and vaccine compositions that can enhance immune response to these underrepresented epitopes are desirable, but not easily attainable. In accordance with the invention, temporary disabling of preexistent antibodies against these epitopes may boost specific immune responses targeting them. This can be achieved by including epitope-derived agents blocking preexistent epitope-specific antibodies into vaccine preparations according to example embodiments described herein.

Minimizing immunoglobulin binding to Fc-receptor-containing cells, including B cells, dendritic cells, monocytes, and macrophages can be achieved in at least two different ways: by blocking the Fc region on the antibodies or by blocking the Fc receptors on target cells. To bind and block the Fc region, non-specific agents such as Protein G or Protein A can be used. Antibodies against the Fc region can also be derived, and Fab fragments (for example, papain-generated and purified fragments) of these antibodies can be used to block the Fc fragment of the original antibody without engaging the Fc receptor on recipient cells. Moreover, nonspecific Fc receptor blocking agents have been developed and are commercially available (for example, Innovex Fc Receptor Blocker). Such agents do not contain immunoglobulins or immunoglobulin fragments, minimizing the possibility of Fc receptor ligation and activation if used in representative vaccine composition embodiments of the invention.

To minimize interaction of the vaccine antigen with the Fab region of preexistent antibodies, antigen-specific and antigen-non-specific blockers can be used. Antigen-specific blockers include, for example, an entire pathogen (live or inactivated), pathogen-related proteins or peptides, and pathogen antigens fused to the molecules of unrelated origin. The latter can serve as "bulking" agents, to increase the possibility of steric hindrance of the specific antigen-binding site, as "sequestration" agents, with the goal to immobilize antigen-specific antibodies in a temporary local depot, sequestering them away from the vaccine antigen, and as larger-scale blockers capable of reaching out to and blocking the Fc region of the same antibody molecule. Antigen-nonspecific blockers can include, for example, molecules binding non-discriminately to and blocking the paratope or the entire Fab region on immunoglobulins, and agents binding to both Fab and Fc Ig fragments.

Blocking of Fab and/or Fc-mediated signaling of preexistent antibodies may need to be achieved simultaneously with the introduction of an antigen into organism. Alternatively, this blocking may need to be effected slightly prior to or after antigen introduction. For simplicity of vaccine administration, a device or method that allows time-delayed release of various vaccine components may be used.

Subject is understood to be any animal or human in need of or capable of receiving prophylactic or therapeutic vaccination.

Vaccine is understood to be a formulation or composition that includes live, killed, inactivated, or attenuated microorganisms, or antigenic proteins (or fragments thereof) obtained from microorganisms. In addition, a vaccine is understood to be a formulation or composition that includes disease-associated proteins (or fragments thereof). The antigenic components of vaccines may be, for example, recombinant or native proteins (or fragments thereof).

Vaccination is understood to mean the introduction of a vaccine into a subject for the purpose of inducing a protective immune response against a particular disease or disorder (that is, an immunizing procedure in which vaccine is administered to a subject). Immunization means the induction of immunity and as used herein specifically means active immunization, which is the stimulation of the immune system to confer protection against a disease or disorder (for example, by administration of a vaccine or toxoid). The terms vaccination and immunization are used interchangeably herein.

Immune response is understood to be an integrated response to an antigen involving recognition of antigens by specific antibodies and previously sensitized lymphocytes (adaptive immune response) and by cells of the innate immune system (innate immune response).

Preexistent immunity is understood to be the presence of antigen-specific antibodies or previously sensitized lymphocytes directed against a pathogen, vaccine delivery vector, or disease-associated proteins (or fragments thereof) at the time of vaccination.

Antigen is understood to be a weakened or killed microorganism (virus or bacterium), parts of the microorganism (native or recombinant), or disease-associated proteins (or fragments thereof, native or recombinant).

Immunosuppression is understood to be the act of reducing the formation of an immune response.

Maternal antibody is understood to be an antibody transmitted from mother to fetus or newborn via the placenta and/or colostrum and breast milk.

Delayed-release device or method is understood to be any device or method capable of releasing an agent or product (for example, a drug or a vaccine) at a time later than that immediately following its administration. Various delayed-release devices have been described (Stubbe et al., Pharm. Res. 21:1732, 2004) and could be applicable to the representative embodiments of the invention. Delayed-release devices and methods can be determined and employed without undue experimentation by one skilled in the art after consideration of all criteria and use of best judgment on the subject's behalf.

Cancer is understood to be an abnormal growth of cells which tend to proliferate in an uncontrolled way and, in some cases, to metastasize.

Autoimmune disorder is understood to be a disorder in which loss of function or destruction of normal tissue arises from humoral or cellular immune responses to the body's own tissue constituents.

Fab means the antigen-binding fragment of any antibody/immunoglobulin. Fab region is understood to be a region on an antibody composed of one constant and one variable domain of each of the heavy and the light chain that binds to antigens.

Paratope is understood to be the antigen-binding site of the Fab region.

Fc (that is, the fragment crystallizable) region is understood to be the tail region of an antibody, composed of the constant domains of the antibody's two heavy chains, which mediates all biologic activities including, for example, binding to some proteins of the complement system and binding to cell surface receptors such as Fc receptors (FcR) and IgE receptors.

Antigen-presenting cell (APC) is understood to be a cell that displays foreign (or abnormal self) antigen complexes with major histocompatibility complex (MHC) on its surface and modulates the activity of other cells during adaptive and innate immune responses.

The vaccines, vaccine compositions, and agents of the embodiments of the invention may, optionally, be administered in combination with (or may include) one or more pharmaceutically acceptable carriers, diluents, or excipients. The vaccines, vaccine compositions, and agents of the embodiments of the invention are administered in an effective amount to induce an immune response to an antigen. Effective amount means a concentration capable of inducing humoral immunity, cell-mediated immunity, or a combination of humoral and cell-mediated immunity in a subject, which is sufficient to cure (partly or completely) or prevent disease or disorder caused by an antigen. One skilled in the art would understand the range of immunological responses anticipated by the terms "humoral immunity" and "cell-mediated immunity," such as antibody production and activities, T cell proliferation and activities, and cytokine production and activities. Such effective amount is understood to be amounts not harmful to the subject where any harmful side effects are outweighed by the benefits. The useful dosage to be administered will vary depending on the age, weight, and type of subject vaccinated, the mode and route of administration, and the type of pathogen against which vaccination is sought.

Optionally, one or more compounds having adjuvant activity may be added to the vaccines or vaccine compositions of the invention. Adjuvants are non-specific stimulators of the immune system. They enhance the immune response of the host to the vaccine. Examples of adjuvants known in the art are Freunds Complete and Incomplete adjuvant, Toll-like receptors (TLRs) and RIG-like receptors (RLRs) ligands and their analogues, vitamin E, non-ionic block polymers, muramyldipeptides, immune stimulating complexes, saponins, mineral oil, vegetable oil, and Carbopol. Adjuvants, especially suitable for mucosal application are, for example, the *E. coli* heat-labile toxin and Cholera toxin. Other suitable adjuvants are, for example, aluminum hydroxide, aluminum phosphate or aluminum oxide, oil-emulsions (for example, of Bayol F® or Marcol 52®), saponins and vitamin-E solubilisate.

Vaccines, vaccination techniques, pharmaceutical compositions, methods of preparing pharmaceutical compositions, and pharmaceutically acceptable carriers, diluents, and excipients are known in the art and are described, for example, in "Remington: The Science and Practice of Pharmacy" (formerly "Remington's Pharmaceutical Sciences," University of the Sciences in Philadelphia, Lippincott, Williams & Wilkins, Philadelphia, Pa. (2005)), the disclosure of which is hereby incorporated by reference.

Any suitable route of administration may be employed for providing a subject with an effective dosage of vaccine, vaccine composition, and agents according to the representative embodiments of the invention. A suitable route of administration may be determined readily by one skilled in the art of pharmacology, immunology, medicine, or the like without undue experimentation. For example, the dosage may be administered orally, intranasally, parenterally, topically, intravenously, intraoccularly, by injection, subcutaneously, or the like. It is understood that injection comprises also perfusion and continuous infusion. Dosage forms may include, for example, tablets, capsules, powders, solutions, dispersions, suspensions, ointments, and aerosols.

It is understood that the vaccine, vaccine composition, and agents according to the present invention are to be administered in pharmacologically or physiologically acceptable amounts, by which is to be understood amounts not harmful to the subject, or amounts where any harmful side effects in individual subjects are outweighed by the benefits. Similarly, the vaccine, vaccine composition, and agents according to the present invention are to be administered in prophylactically or therapeutically effective amounts, which are to be understood as amounts meeting the intended prophylactic or therapeutic objectives, and providing the benefits available from administration of such vaccine, vaccine composition, and agents.

The dosage ranges for administration of the vaccine, vaccine composition, and agents according to the present invention are those which produce the desired effect(s). For example, an effective amount of vaccine refers to the amount administered to achieve seroconversion and is evidenced such as by the presence of, for example, a two- to four-fold higher level of antigen-specific antibodies in the subject's serum. The dosage will vary generally with the age, weight, and response of the individual subject. The dosage will also vary with the nature or the severity of the underlying condition, with epidemiologic conditions, with the concomitant use of other active compounds, and the route of administration. In addition, the dosage will be determined by the existence of any adverse side effects such as local hypersensitivity, systemic adverse effects, and immune tolerance.

An effective dose of the antigen (and agent(s)) can be determined without undue experimentation (for example, by pharmacokinetic studies) by one skilled in the art after consideration of all criteria and use of best judgment on the patient's behalf. In one representative embodiment, live RSV (the antigen) is administered at dose levels from about $10^{3.5}$ to about $10^{4.5}$ pfu; UV-inactivated RSV (the agent) is administered at dose levels equivalent to live RSV doses from about $10^{3.5}$ to about $10^{4.5}$ pfu; Streptococcal Protein G is administered at dose levels from about 200 to 300 μg/kg of subject weight. It is anticipated that a mixture of an antigen and agent(s) may be administered, for example, intramuscularly (i.m.) in a minimum volume of 0.5 ml of normal saline.

The following example is provided for illustration purposes only, and is in no way intended to limit the scope of the present invention.

EXAMPLE

Overcoming the Immunosuppressive Effect of Preexistent Immunity on Intramuscular Vaccination with Live Respiratory Syncytial Virus (RSV)

Rationale and Basic Experimental Approach

Intramuscular (i.m.) vaccination with live Respiratory Syncytial Virus (RSV) was selected for proof of concept studies. In RSV seronegative humans, vaccination with live virus i.m. is highly efficient. In contrast, vaccination efficacy is dramatically reduced in individuals with preexistent immunity to RSV. The cotton rat *Sigmodon hispidus* is a proven animal model of RSV infection in general and of live RSV i.m. vaccination in particular. Similar to humans, cotton rats immunized with live RSV i.m. are protected against subsequent RSV infection, while the efficacy of i.m. live RSV vaccination is dramatically reduced in animals infused with anti-RSV serum prior to vaccination.

To overcome the immunosuppressive effect of preexistent antibodies on vaccination with live RSV, UV-inactivated RSV was chosen as the agent destined to occupy/block paratopes on anti-RSV antibody and Protein G was chosen as the agent for blocking the Fc fragment on IgG. UV-inactivated RSV and Protein G were included in a vaccine formulation containing live RSV. The mixture was used to intramuscularly immunize animals infused with hyperimmune anti-RSV serum. Animals were subsequently challenged with RSV to assess the strength of antiviral immunity generated by vaccination.

Materials and Methods

RSV A/Long was used for the vaccine formulation and challenge studies. PBS, pH 7.4 was used as a diluent.

The following vaccine formulations were tested (per 50 μl vaccine dose):

(a) Live RSV alone ($10^4$ pfu live RSV), (b) Live RSV in combination with Protein G and UV-inactivated RSV ($10^4$ pfu live RSV+25 μg Protein G+UV-inactivated RSV (an equivalent of $10^4$ pfu RSV), (c) Live RSV in combination with Protein G ($10^4$ pfu live RSV+25 μg Protein G), and (d) Live RSV in combination with UV-inactivated RSV ($10^4$ pfu live RSV+UV-inactivated RSV (an equivalent of $10^4$ pfu RSV).

The prototype Long strain of RSV was obtained from American Type Culture Collection (Manassas, Va.). Virus was propagated in HEp-2 cells and serially plaque-purified to reduce defective-interfering particles. Recombinant Protein G was obtained from Calbiochem (catalog number 539303) and contained <0.1 EnU/mg.

Twenty-four hours prior to vaccination, cotton rats were injected intraperitoneally (i.p.) under isoflurane anesthesia with 200 μl control serum previously collected from naive cotton rats or with 200 μl hyperimmune anti-RSV serum (titer 1:2,600) collected from RSV convalescent rats. On the day of vaccination, an appropriate vaccine formulation was injected i.m. under isoflurane anesthesia into the right quadriceps muscle (50 μl per animal). Twenty days later animals were infected intranasally under isoflurane anesthesia with $10^5$ pfu live RSV per animal in 100 μl. Cotton rats were sacrificed on day 4 post-infection and lungs were collected for analysis of viral load by plaque assay. Serum was collected for antibody measurement on day 1, 14, and 28 post-infection.

Results

Figure 2:
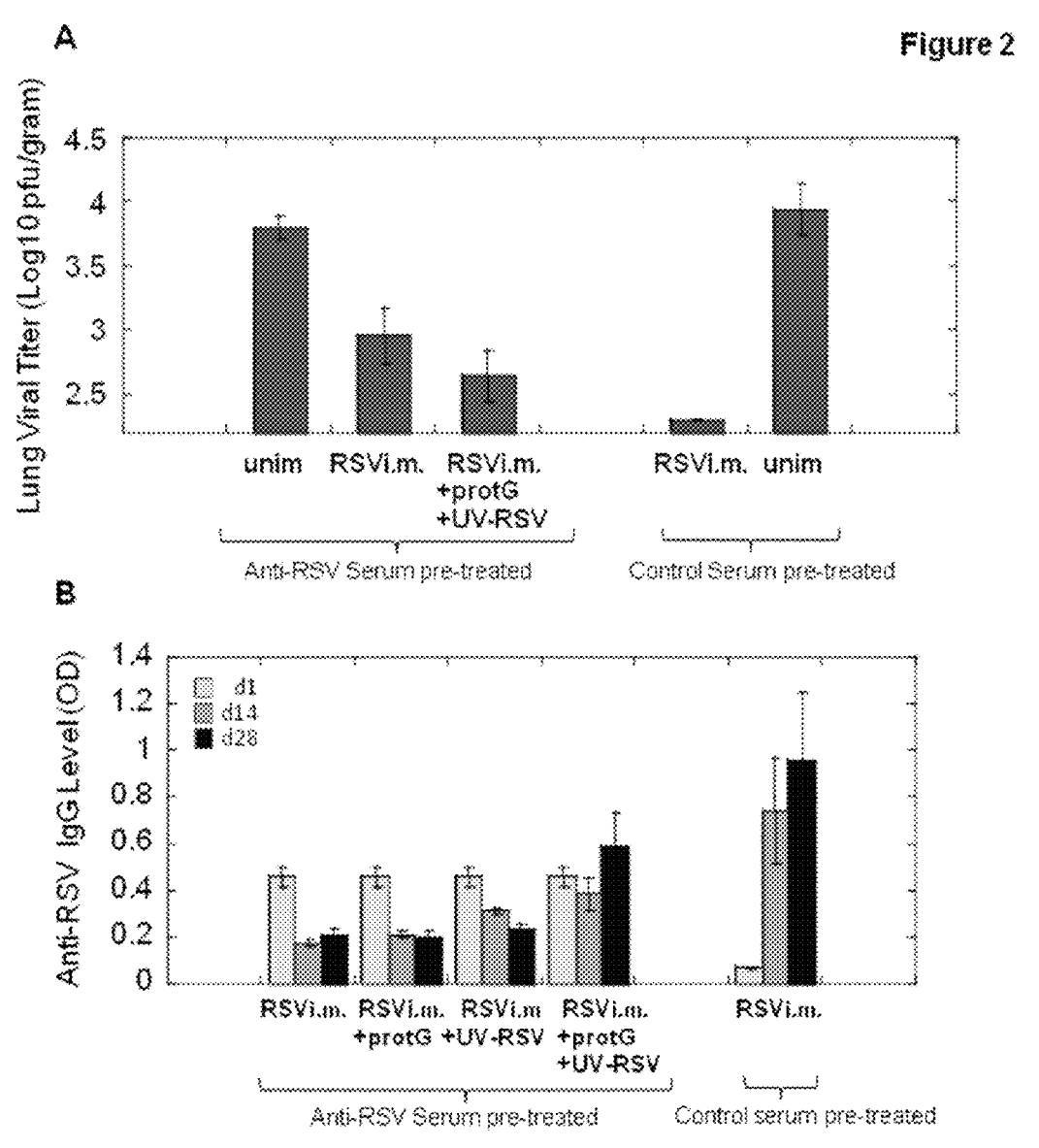

The presence of anti-RSV serum reduced the efficacy of i.m. vaccination with live RSV. Higher number of animals vaccinated i.m. with live RSV in the presence of anti-RSV serum showed detectable viral replication in the lungs compared to animals vaccinated with live RSV i.m. in the absence of anti-RSV serum (Table 1). Higher average pulmonary RSV titer was detected in animals that received live RSV i.m. in the presence of anti-RSV serum (FIG. 2A). Inclusion of Protein G and UV-inactivated RSV into the live RSV vaccine formulation increased the number of animals per group that were protected from RSV replication after subsequent RSV challenge (Table 1). The effect was consistent in two independent experiments. A moderate reduction in the mean pulmonary viral titer was also observed (FIG. 2A).

The beneficial effect of the inclusion of Protein G and UV-inactivated RSV in the vaccine formulation was also seen when the levels of RSV-specific IgG after vaccination were measured. Animals vaccinated with live RSV i.m. in the absence of antibody pretreatment mounted a strong specific anti-RSV response, with a pronounced increase in antibody titer visible between day 1 and day 14, and a further moderate increase between day 14 and day 28 (FIG. 2B). Animals pre-treated with high titer RSV-specific sera and vaccinated i.m. with live RSV could not generate anti-RSV IgG beyond the level already present on day 1 and a significant drop in antibody level was seen between day 1 and day 14, with the level remaining low on day 28. In animals vaccinated with a mixture of live RSV, Protein G and UV-inactivated RSV, a moderate increase in the level of anti-RSV IgG was seen between day 14 and day 28, indicating generation of new RSV-specific antibodies. Addition of Protein G or UV-inactivated RSV alone did not improve the efficacy of vaccination or antibody generation, indicating that a synergistic effect between the two agents may be required for improved vaccination.

In summary, the efficacy of vaccination against a particular antigen is significantly reduced by the presence of preexistent antigen-specific antibodies which suppress de novo antibody production. Overcoming the immunosuppressive effect of preexistent antibodies can be achieved by inclusion of additional agents into the vaccine formulation including, for example, (1) at least one agent capable of binding to and/or blocking the antigen-recognition site of preexistent antibodies and/or (2) at least one agent capable of binding to and/or blocking the Fc fragment of preexistent antibodies or Fc receptors on Fc receptor-bearing cells. With the antigen-recognition and Fc-mediated mechanisms temporarily disabled, sequestered, and/or suppressed, the vaccine antigen is able to initiate an efficient antigen-specific immune response, including de novo production of antigen-specific antibodies.

Each reference referred to within this disclosure is hereby incorporated in its respective entirety.

Having now described a few embodiments of the invention, it should be apparent to those skilled in the art that the foregoing is merely illustrative and not limiting, having been presented by way of example only. Numerous modifications and other embodiments are within the scope of one of ordinary skill in the art and are contemplated as falling within the scope of the invention and any equivalent thereto. It can be appreciated that variations to the present invention would be readily apparent to those skilled in the art, and the present invention is intended to include those alternatives. Further, because numerous modifications will readily occur to those skilled in the art, it is not desired to limit the invention to the exact construction and operation illustrated and described, and accordingly, all suitable modifications and equivalents may be resorted to, falling within the scope of the invention.

TABLE 1

Pulmonary Replication of RSV in Cotton Rats Immunized with Live RSV in the Absence/Presence of Protein G and/or UV-Inactivated RSV.

| Pre-treatment | Vaccination | Experiment 1 Viral Titer[a] | Experiment 1 Virus not detectable[b] (animals/group) | Experiment 2 Viral Titer | Experiment 2 Virus not detectable (animals/group) |
|---|---|---|---|---|---|
| Anti-RSV Serum[c] | RSV i.m. | 3.90 | 1/5 | 3.15 | 1/5 |
| | | 3.73 | | 3.53 | |
| | | 3.15 | | 3.2 | |
| | | 2.78 | | 2.6 | |
| | | <2.30 | | <2.3 | |
| | RSV i.m. + Protein G + UV-RSV | 3.56 | 3/5 | 3.08 | 3/5 |
| | | 4.06 | | 3.2 | |
| | | <2.3 | | <2.3 | |
| | | <2.3 | | <2.3 | |
| | | <2.3 | | <2.3 | |

TABLE 1-continued Pulmonary Replication of RSV in Cotton Rats Immunized with Live RSV in the Absence/Presence of Protein G and/or UV-Inactivated RSV.

| Pre-treatment | Vaccination | Experiment 1 Viral Titer[a] | Experiment 1 Virus not detectable[b] (animals/group) | Experiment 2 Viral Titer | Experiment 2 Virus not detectable (animals/group) |
|---|---|---|---|---|---|
| | RSV i.m. + Protein G | 3.72<br>3.97<br>3.38<br>3.81<br>3.82 | 0/5 | — | |
| | RSV i.m. + UV-RSV | 4.26<br>4.48<br>4.26<br>3.83<br>3.96 | 0/5 | — | |
| | No vaccine | — | | 3.89<br>3.88<br>3.53<br>3.72<br>3.96 | 0/5 |
| Control Serum | RSV i.m. | 3.1<br>2.6<br><2.3<br><2.3<br><2.3 | 3/5 | <2.3<br><2.3<br><2.3<br><2.3<br><2.3 | 5/5 |
| | No vaccine | 5.00<br>4.92<br>5.03<br>4.62<br>5.15 | 0/5 | 4.64<br>3.83<br>3.69<br>4.00<br>3.56 | 0/5 |

[a]$Log_{10}$ pfu/gram. Cotton rats were challenged with $10^5$ pfu RSV A/Long per animal 28 days after immunization with $10^4$ pfu live RSV i.m. per animal.
[b]Viral replication was assessed by plaque assay with the limit of detection of 2.3 pfu/gram of lung tissue.
[c]Cotton rats were inoculated i.p. with 0.2 ml anti-RSV serum (titer 1:2600) 24 hours prior to immunization.

We claim:

1. A method of vaccination against respiratory syncytial virus (RSV) in an animal or human, comprising:
   (a) administering a vaccine, and
   (b) administering at least one agent that binds to preexistent antibodies directed to the antigenic component of said vaccine, wherein said at least one agent is selected from the group consisting of recombinant Protein A, native Protein A, recombinant Protein G, native Protein G, recombinant Protein A/G, native Protein A/G, and ultraviolet light-inactivated RSV,
whereby the immunosuppressive effect of said preexistent antibodies on said vaccination is circumvented.

2. The method of claim 1, wherein said vaccine is administered before said at least one agent.

3. The method of claim 1, wherein said at least one agent is administered before said vaccine.

4. The method of claim 1, wherein said at least one agent is administered within 24 hours before vaccine.

5. The method of claim 1, wherein said vaccine and said at least one agent are administered simultaneously.

6. The method of claim 1, wherein said vaccine is administered by a delayed-release device or method.

7. The method of claim 1, wherein said at least one agent is administered by at least one delayed-release device or method.

8. The method of claim 1, wherein said vaccine and said at least one agent are administered by at least one delayed-release device or method.

* * * * *